United States Patent [19]

Ellard et al.

[11] 4,421,913

[45] Dec. 20, 1983

[54] SEPARATION OF TRIPHENYLPHOSPHINE OXIDE FROM METHOTREXATE ESTER AND PURIFICATION OF SAID ESTER

[75] Inventors: James A. Ellard; James A. Webster, both of Dayton, Ohio

[73] Assignee: The United States of America as represented by the Secretary of the Department of Health and Human Services, Washington, D.C.

[21] Appl. No.: 329,869

[22] Filed: Dec. 11, 1981

Related U.S. Application Data

[63] Continuation of Ser. No. 143,129, Apr. 23, 1980, abandoned.

[51] Int. Cl.$^3$ .......................................... C07D 475/08
[52] U.S. Cl. ................................................... 544/260
[58] Field of Search ........................................ 544/260

[56] References Cited

U.S. PATENT DOCUMENTS 4,079,056  3/1978  Piper et al. ........................... 544/260
4,080,325  3/1978  Ellard .................................. 544/260

Primary Examiner—Paul M. Coughlan, Jr.
Attorney, Agent, or Firm—John S. Roberts, Jr.

[57] ABSTRACT

An improvement in the production of methotrexate as set out in Ellard U.S. Pat. No. 4,080,325. It has been found that magnesium oxide facilitates the coupling reaction by acting as an acid acceptor. The dense grade of magnesium oxide is preferred in molar proportions of 2 to 4 moles of magnesium oxide per mole of 2,4-diamino-6-hydroxymethylpteridine. Further, the triphenylphosphine oxide which is generated by hydrolysis of the protecting groups is removed from the reaction stream by utilization of toluene or BTX-type solvents.

2 Claims, No Drawings

SEPARATION OF TRIPHENYLPHOSPHINE OXIDE FROM METHOTREXATE ESTER AND PURIFICATION OF SAID ESTER

This is a continuation of application Ser. No. 143,129, filed Apr. 23, 1980, now abandoned.

The invention described herein was made in the course of work under a contract from the Department of Health, Education, and Welfare.

The present invention is concerned with two process improvements which may be applied to the basic Ellard U.S. Pat. No. 4,080,325, which dealt with the coupling of diethyl-N-[4-(methylamino)benzoyl]-L-glutamate with a 6-bromomethyl-2,4-diaminopteridine derivative to form diethyl methotrexate. This latter compound, upon hydrolysis of the ethyl ester groups, releases the free compound, methotrexate. Ellard U.S. Pat. No. 4,080,325 is incorporated by reference in its entirety for the closely related subject matter of this application.

PRIOR ART STATEMENT

U.S. Pat. No. 4,080,325 Ellard
U.S. Pat. No. 4,077,957 Piper/Montgomery
U.S. Pat. No. 4,079,056 Piper/Montgomery In the Ellard patent the coupling with the glutamate is assisted by the present acid acceptor magnesium oxide. Also, the triphenylphosphine present as an imine derivative is used as a protecting group in the process and is later removed from the molecule by hydrolysis after coupling with glutamate. U.S. Pat. No. 4,080,325 Ellard has won recognition as the Ellard procedure for preparation of methotrexate.

As to the Piper/Montgomery patents, these patents are relevant and in some cases parallel the Ellard work but are not deemed as pertinent as Ellard discussed above.

ADDITION OF MAGNESIUM OXIDE TO THE CHARGE IN THE METHOTREXATE PROCESS

It has been found that, uniquely enough, of the available alkaline earth oxides and alkali metal oxides, the presence of magnesium oxide in a preferred amount of 2 to 4 moles per mole of 2,4-diamino-6-hydroxymethylpteridine assists in the production and recovery at higher levels than would ordinarily be obtained.

It is noted that, of the available magnesium oxides, the heavy magnesium oxide which is insoluble in water, is preferred over light magnesium oxide which reacts with water to form milk of magnesia. The magnesium oxide is utilized as an acid acceptor.

The use of the proper grade of magnesium oxide has also been found to control unanticipated exothermal reaction where a temperature excursion had been experienced in the methotrexate process.

In the process the use of a dense form of magnesium oxide as an acid acceptor resulted in an accelerated coupling reaction, which, though exothermic, is easily controlled.

ELIMINATION OF TRIPHENYLPHOSPHINE OXIDE BY-PRODUCT

The bulk of triphenylphosphine oxide formed upon quenching a reaction mixture normally precipitates from aqueous quench solution and is removed by filtration. That some phosphine oxide remains in solution and is carried on through the ester hydrolysis step was recognized early on.

A toluene extraction of an aliquot of aqueous solution of methotrexate (MTX) following the hydrolysis step showed a surprisingly high phosphine oxide content, about 12% of the MTX content, although much of this is removed by charcoal treatment and subsequent filtration at pH 7. Addition of toluene to the acidified water to be used for quench of coupling reaction solution and quenching into this two-phase system was found to effect removal of the phosphine oxide from the aqueous solution of methotrexate ester. As alternatives to utilization of toluene, the so-called BTX solvents (benzene-toluene-xylene) may be utilized for the extraction.

In addition, an ester purification procedure has been developed which consists of filtering the ester after it has been dissolved in acidic ethanol. A preferred filter is a Sparkler filter packed with Pre-Co-Floc plus a 1 micron Filterite cartridge and a 1 micron (absolute) Pall filter. An alcohol solution is passed through a pressure filter containing cellulosic filter aid and followed by a filter cartridge containing a cellulosic filter element, the filter aid and the filter cartridge having previously been moistened with an aqueous acid solution. The aqueous acid solution preferentially removes basic polar impurities from the alcohol solution without removing the methotrexate ester.

EXAMPLE 1

Recovery of Crude Methotrexate Ester (MTXE)

A modified quench procedure was used for couplings 17, 18, and 19 pursuant to the description at column 4 of U.S. Pat. No. 4,080,325 Ellard. Quenching normally hydrolyzes the triphenylphosphinyl derivatives to triphenylphosphine oxide which is separated as an insoluble solid from the aqueous dimethylacetamide (DMAC) solution of methotrexate ester. This separation has been incomplete inasmuch as the MTX ester has had triphenylphosphine oxide contents as high as 15%. In some cases, MTXE coprecipitated with the triphenylphosphine oxide as well.

Laboratory experiments with the high yield coupling (Batch 16) showed that effective, high-yield separation of MTXE from triphenylphosphine oxide could be achieved by quenching into a two phase mixture of toluene and acidified water. The triphenylphosphine oxide partitions into the toluene while the MTX ester remains in the aqueous phase. In the experimentation of this example, there were a total of 3 batches which had somewhat different results.

In superior results, Batch 18 and Batch 19 couplings were also quenched into toluene/water. Here a clean separation of toluene/triphenylphosphine oxide phase from the methotrexate ester was followed by precipitation of the crude MTXE from aqueous solution as an easily filtered product.

EXAMPLE 2

Ester Purification

As a step to purify the MTXE from impurities, including pteridines and triphenylphosphine oxide, it is possible to remove these impurities by filtering the ester after it has been dissolved in acidic ethanol. A preferred filter for this use is a Sparkler filter packed with Pre-Co-Floc plus a 1 micron Filterite cartridge and a 1 micron (absolute) Pall filter. As a pre-preparation, it has been found that the filter string should be washed with about 1 gallon of 1.0 N HCl in water before use. This treatment causes the Pre-Co-Floc to function much more efficiently, thus trapping the majority of the impurity in the Sparkler filter and not blinding the other two filter cartridges. In summary, the ester is filtered after it has been dissolved in acidic ethanol.

EXAMPLE 3

B-18 Coupling

In this run the amount of 2,4-diamino-6-hydroxymethylpteridine hydrobromide (Intermediate III HBr) used was based on analysis of the purity of the material. The amount of bromine and triphenylphosphine was also adjusted in accordance with the amount of water that was present in the starting materials.

The batch was run using the folowing amount of reagents:

|  | Normal | Actual |
| --- | --- | --- |
| Triphenylphosphine | 272 lbs. | 364 lbs. |
| Bromine | 166 | 222 |
| Int III HBr | 88.5 | 108 |
| Int VI | 120 | 120 + 18 |
| Magnesium Oxide | 35 | 35 + 7 |

Int III HBr = 2,4-diamino-6-hydroxymethylpteridine hydrobromide
Int VI = Diethyl N—[(p-methylamino)benzoyl]-L—glutamate After the initial reaction period, analysis indicated a deficiency in Int VI and thus six additional pounds were added and the batch allowed to stir over the weekend. After two days reaction time, the reaction was still incomplete and lab experiments showed that additional magnesium oxide would drive the reaction closer to completion. Therefore, seven additional pounds of magnesium oxide and twelve more pounds of Int VI were added to the batch and allowed to react for 24 more hours.

In this example a new quench procedure was utilized by quenching the coupling mixture into a mixture of toluene and water. The pH of the toluene/water mixture was adjusted to about 0.6. A portion of the reaction mixture was added to the stirred solution and then the layers were allowed to separate. The lower phase contained the water and MTX ester in solution and was easily drained off while the toluene layer contained only phosphine oxide. The toluene layer was quickly drained off. There was little or no emulsion layer between the two phases and a clean separation was obtained. The MTX ester now contained only about 1% phosphine oxide, whereas the amount of phosphine oxide in the previous techniques ranged up to 15%.

The well-known Ellard process is exemplified by U.S. Pat. No. 4,080,325 Ellard and claim 1 of the patent sets out the steps for preparing methotrexate as follows: (a) reacting tetraaminopyrimidinehydrochloride with dihydroxyacetone in the presence of air and water and at a pH in the range of 5.5±0.2 to give 2,4-diamino-6-hydroxy-methylpteridine; (b) converting the 2,4-diamino-6-hydroxy-methylpteridine to the hydrobromide salt, namely, 2,4-diamino-6-hydroxymethylpteridine hydrobromide salt; (c) reacting the 2,4-diamino-6-hydroxymethylpteridine hydrobromide salt with triphenyldibromophosphorane to give 2,4-bis(triphenylphosphazine)-6-bromomethylpteridine hydrobromide; (d) reacting the 2,4-bis(triphenylphosphazino)-6-bromomethylpteridine hydrobromide with ethyl N-(p-methylamino)benzylglutamate to give the phosphazino derivative of methotrexate ester; (e) hydrolyzing the phosphazino derivative of methotrexate ester to give triphenylphosphine oxide and methotrexate ester; and (f) hydrolyzing the methotrexate ester to give methotrexate.

We claim:

1. In the preparation of methotrexate by the Ellard process, which involves the coupling of dimethyl-N-[4-(methylamino)-benzoyl]-L-glutamate with a 6-(bromomethyl)-2,4-diamino-pteridine derivative to form the methotrexate ester, and further in a step involving the quenching and separation of the methotrexate ester, utilizing a biphase solution and the use of an organic solvent selected from the group consisting of benzene, toluene, and xylene to form a two-phase system wherein the methotrexate ester is recovered in the aqueous phase and a byproduct triphenylphosphine oxide is separated and recovered in the organic solvent.

2. In the preparation of methotrexate according to claim 1 wherein the organic solvent is toluene.

* * * * *